United States Patent
Boyd et al.

(10) Patent No.: US 7,887,495 B2
(45) Date of Patent: Feb. 15, 2011

(54) PROTECTIVE AND COSMETIC COVERING FOR EXTERNAL FIXATORS

(76) Inventors: Lawrence M. Boyd, 25 Birnham La., Durham, NC (US) 27707; Douglas Kirven, 511 Clayton Rd., Durham, NC (US) 27703; Samuel B. Adams, 1216 Orchard Oriole La., Durham, NC (US) 27713

( * ) Notice: Subject to any disclaimer, the term of this patent is extended or adjusted under 35 U.S.C. 154(b) by 190 days.

(21) Appl. No.: 12/253,315

(22) Filed: Oct. 17, 2008

(65) Prior Publication Data
US 2009/0105621 A1    Apr. 23, 2009

Related U.S. Application Data

(60) Provisional application No. 60/980,819, filed on Oct. 18, 2007.

(51) Int. Cl.
*A61F 5/00* (2006.01)
*A61F 5/04* (2006.01)
*A43B 3/02* (2006.01)

(52) U.S. Cl. .............. 602/3; 606/54; 36/7.1 R

(58) Field of Classification Search ........ 2/61, 2/239, 242, 22, 23, 241; 602/3, 62, 63; 36/702, 36/8.1, 110, 7.1 R; 606/54, 53, 1
See application file for complete search history.

(56) References Cited

U.S. PATENT DOCUMENTS 3,735,759 A * 5/1973 MacKay ............ 602/3
6,047,403 A * 4/2000 Juozaitis ............ 2/61
6,405,731 B1 * 6/2002 Chiang ............ 128/878

FOREIGN PATENT DOCUMENTS

FR    2630908 A1 * 11/1989

OTHER PUBLICATIONS

Translation of foreign patent No. FR002630908A1.*

\* cited by examiner

*Primary Examiner*—Patricia M Bianco
*Assistant Examiner*—Tarla R Patel
(74) *Attorney, Agent, or Firm*—Maginot, Moore & Beck LLP

(57) ABSTRACT

A removable protective covering is provided that can be secured about an external fixation device on the upper or lower extremity of a patient. The covering includes a fabric form that is sized and configured to accommodate varying sizes of external fixation devices and uses readily engageable/releasable closure elements or fasteners to securely engage the covering about the fixator and the extremity. A drawstring closure may be provided at the open ends of the covering to tighten the end about the patient's limb. Ventilation features may be provided including vents with and without additional devices to generate air flow through the covering. The covering for a lower extremity fixation device may be configured for removably attachment to a foot plate and the foot plate itself may be configured to support or attach to the fixation device.

9 Claims, 8 Drawing Sheets

PROTECTIVE AND COSMETIC COVERING FOR EXTERNAL FIXATORS

CROSS-REFERENCE TO RELATED APPLICATION

The present application claims priority to co-pending provisional application No. 60/980,819, entitled "Protective and Cosmetic Covering for External Fixators", filed on Oct. 18, 2007, the disclosure of which is incorporated herein by reference.

BACKGROUND

The present invention relates generally to a device for covering and protecting external fixation devices. External fixation devices are used for stabilization of bony elements in order to allow for bone healing following a fracture or dislocation. These external fixation devices may also be utilized following a surgical realignment of the bones (osteotomy) as well as for intentional fusion of arthritic joints. Typically, the devices are engaged to the peripheral skeletal structures. The invention contemplates devices and methods for providing a protective and cosmetic covering to the external fixation device.

An external fixation device is a stabilization system consisting of a system of threaded and smooth pins fixed to the bony elements which are then anchored to a ring or bar structure for stabilization. Rods are used to link the ring elements and provide for stability between the elements during healing. External fixators F are very bulky, as shown in FIGS. 1 and 2 (for the lower extremity) and FIGS. 3 and 4 (for the upper extremity). When used for definitive skeletal fixation or joint fusion, these structures are applied to the skeletal elements for long lengths of time, typically ranging from six weeks to six months. If the structure is placed on the lower limb and incorporates the boney elements of the foot, provision may be made for ambulation by attachment of a base plate and rubber sole or a modified shoe to the fixation system. However, no provision is made for any external covering to the fixation system.

Currently, coverings are can be provided for plaster casts that may be applied to the skeletal system. Casts are smaller and lower profile and more easily provided with a fabric covering. These coverings may be commercially available or may be easily fabricated by the patients. It may even be possible to utilize a large sock to cover the plaster cast. Where the cast is applied to the lower limb, a walking cast may incorporate a rubber insert into the plaster or a separate fabric boot B held by VELCRO® straps that wrap around the cast, as depicted in FIG. 5. Specialized coverings have been designed to allow for water-proofing of the plaster, as shown in FIG. 6.

A covering entity for an external fixator would provide for multiple benefits to the patient. First, the external fixation system is not aesthetically appealing and a covering would give both adult and pediatric patients an enhanced personal image by covering the pins protruding from the skin and the unsightly framework of the fixation system. Patients may be reluctant to be in public view with the complex fixation elements protruding from their upper or lower limbs. Pins protruding openly from the skin and the complex fixation frame are a likely source of unwanted attention in public. Especially in the pediatric population, the embarrassment of the presence of the external fixation system may lead to distress in peers in school point to the device and ask questions. For children, the opportunity to cover the device would be of great benefit.

Secondly, a protective covering can provide enhanced patient comfort from nature's elements, such as cold or wet conditions. Third, a covering may act to reduce the likelihood of infection along the pin tracks, a well recognized complication of external fixation devices. Moreover, a covering for the external fixator F will preserve the durability of the fixation element anchorage and any skin bandages associated with the implantation of the fixator. Given the long duration of the fixation time, the fixator and instrumentation site are exposed daily to a variety of debris. Bacterial contamination from airborne particles, as well as debris or spills, may travel along the fixation system and reside at the skin-implant interface. Pin tract infections are a serious complication, requiring local debridement and potentially removal of all or part of the infected fixation device prior to its intended duration of treatment. Reducing exposure of the fixator and skin interface will greatly reduce the risk of these complications.

What is needed is a protective covering that meets all of these desirable qualities and that is easily used by the patient.

SUMMARY

To address this need, a removable covering is provided that can be secured about an external fixation device on the upper or lower extremity of a patient. The covering protects the fixation device while providing an aesthetic improvement to the limb while it mends. The covering includes a fabric form that is sized and configured to accommodate varying sizes of external fixation devices and uses readily engageable/releasable closure elements or fasteners to securely engage the covering about the extremity. In some embodiments, a drawstring closure may be provided at the open ends of the covering to tighten the end about the patient's limb.

In other embodiments, ventilation features may be provided including vents with and without additional devices to generate air flow through the covering. In another embodiment of the invention, the covering for a lower extremity fixation device is configured to be removably attached to a foot plate. The foot plate itself may also be configured to support components of the fixation device.

DESCRIPTION OF THE ILLUSTRATED EMBODIMENTS

Figure 1:
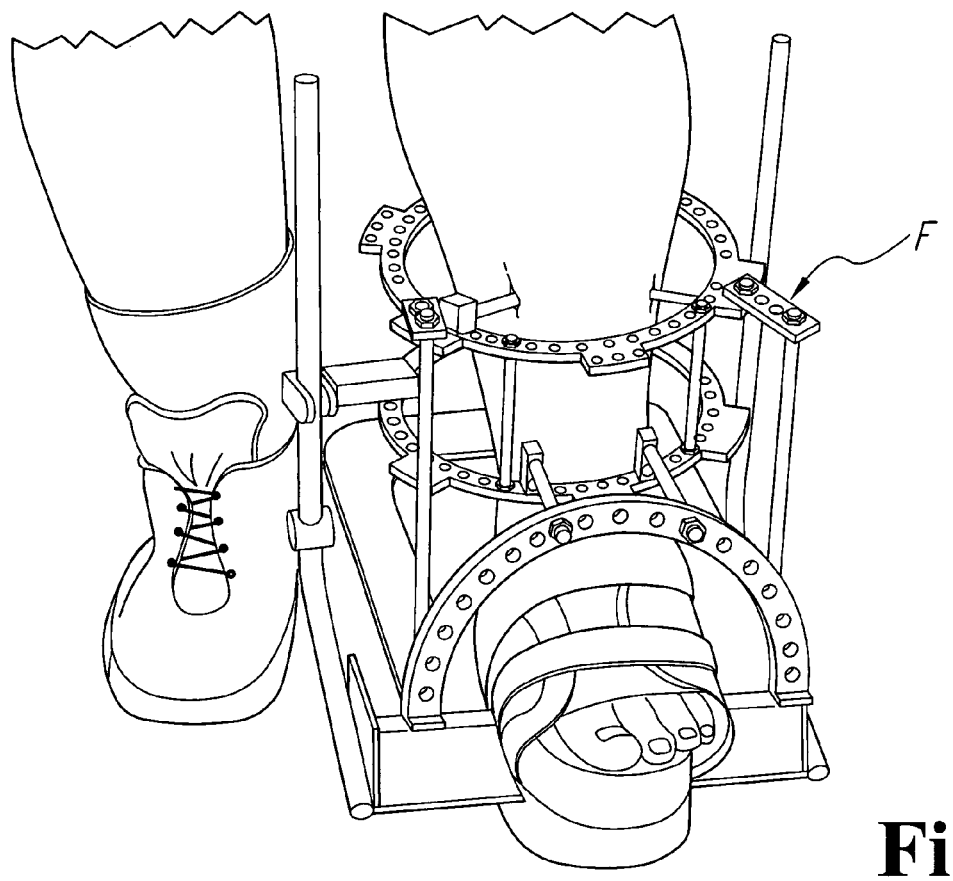
FIG. 1 shows one form of an external fixation system affixed to the lower limb, with a heel insert attached to the system.
Figure 2:
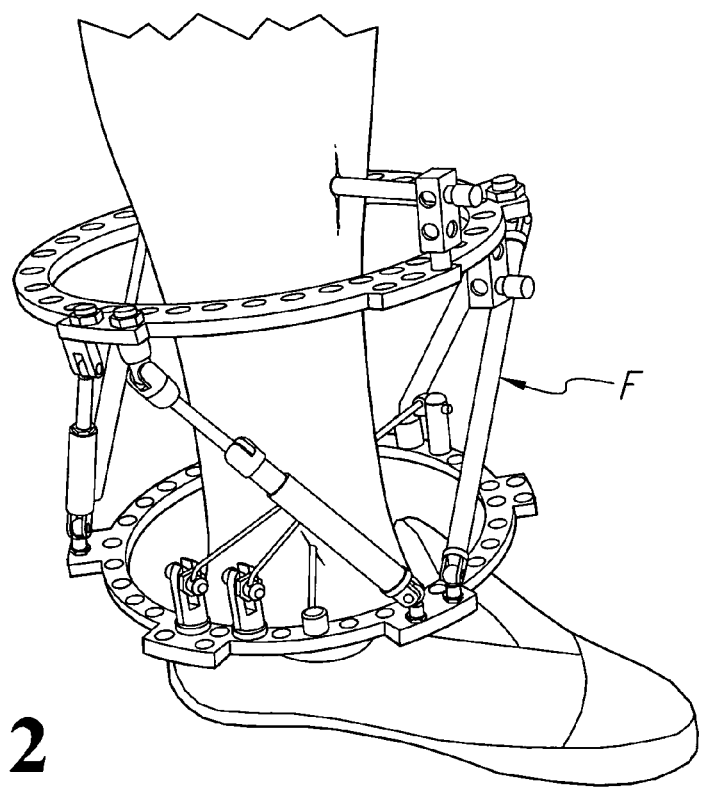
FIG. 2 shows another external fixation system affixed to the lower limb without a heel insert.
Figure 3:
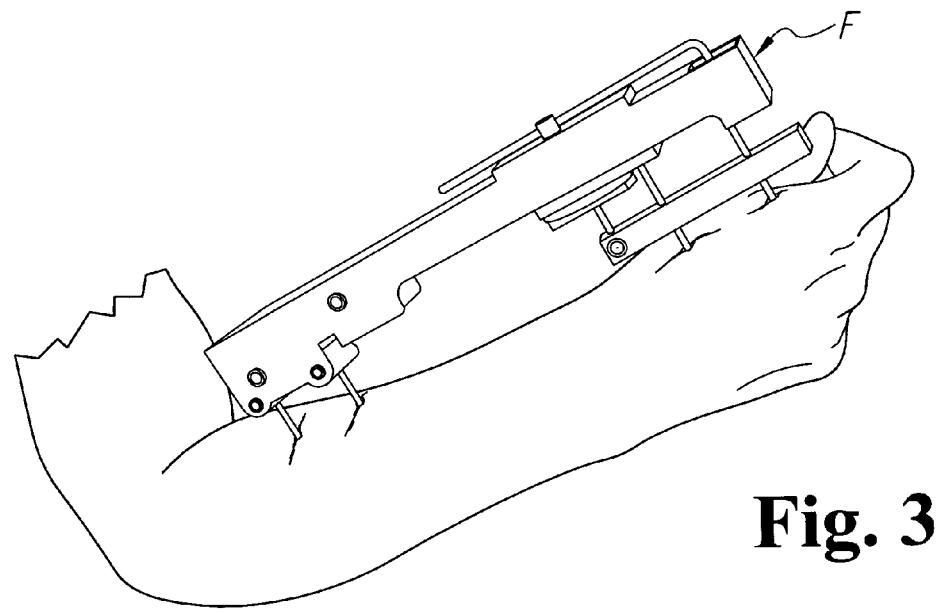
FIGS. 3 and 4 depicts external fixators applied to the upper limbs
Figure 4:
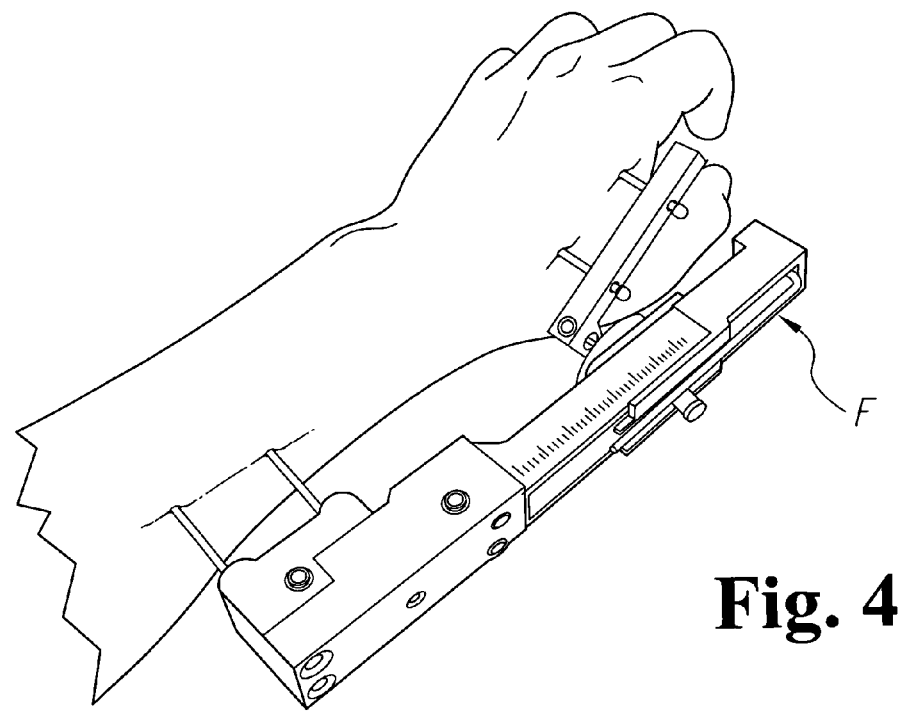
Figure 5:
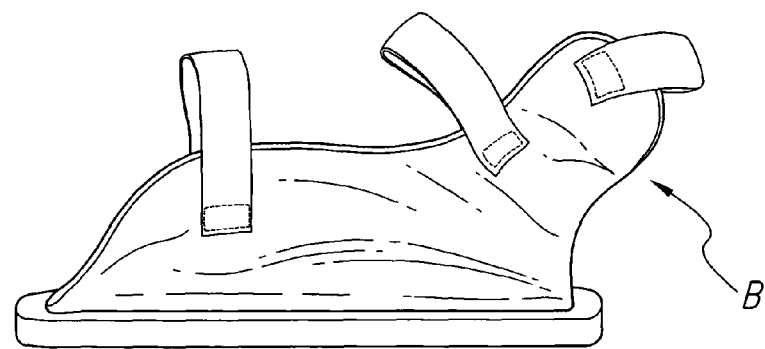
FIG. 5 shows a cast covering for the lower limb used to allow walking.
Figure 6:
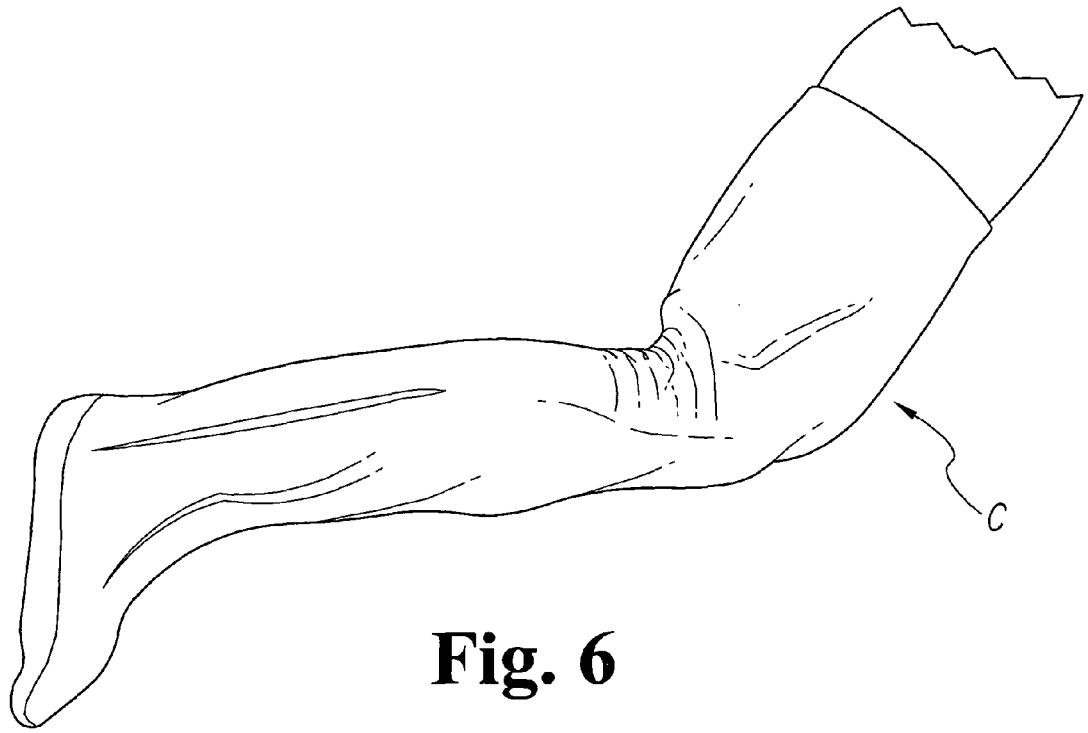
FIG. 6 illustrates a waterproof cast covering.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 7:
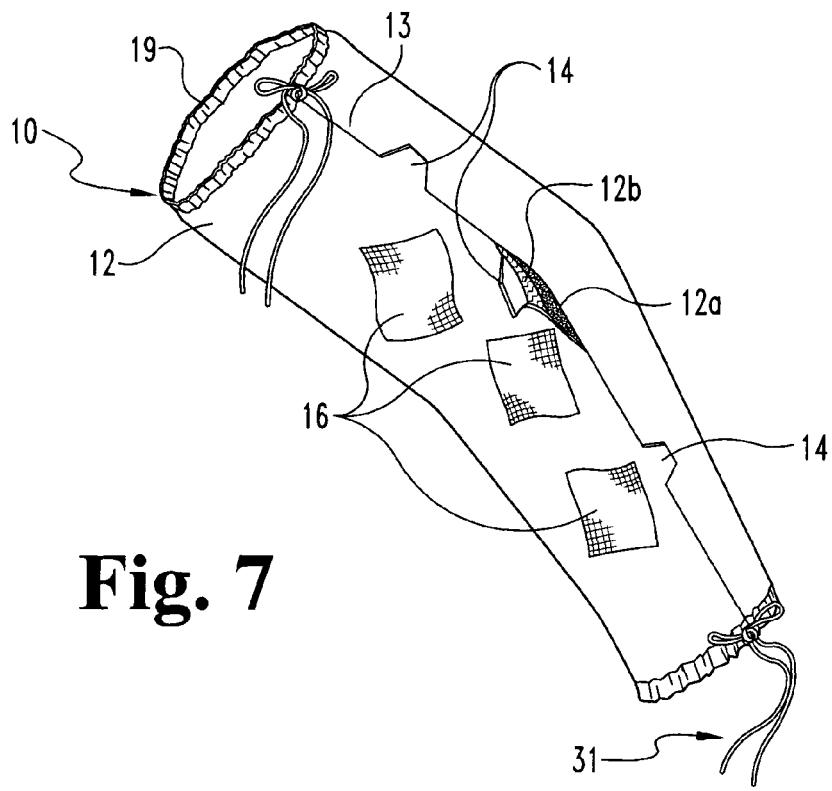
FIG. 7 is a perspective view of a protective and cosmetic covering according to one disclosed embodiment for use with an external fixator placed on a lower or upper limb.

The present invention contemplates a device that is used following fixation of an external fixation element to the upper or lower skeletal system. In one embodiment, a covering for external fixators is sized and configured to be secured about an external fixator devices attached to the upper or lower limb. In the upper limb, fixation may be to the humerus, radius, ulna, carpal, metacarpal, and phalangeal bones. For upper limb fixation a covering 10, shown in FIG. 7, is sized and configured to cover a fixation ring and/or bar elements ranging the gamut of bone sizes in the human population. In the lower limb, fixation may be applied to the femur, tibia, fibula, tarsal, metatarsal and phalangeal bones. For these procedures, a covering 20, shown in FIG. 8, is sized and configured to cover a fixation ring and/or bar elements ranging the gamut of these bone sizes in the human population.

Given the wide range of sizes available for external fixator devices, location of these devices, and sizes of bones applied to, it can be anticipated that a size-adjustable covering may be preferred in order to limit inventory required by the hospital or clinic. Thus, in one aspect of the embodiments, the cover may be expandable and collapsible with closure elements or fasteners including, but not limited to, zippers, snaps, buttons, drawstrings, or hook and loop type fasteners (such as VEL-CRO®) to accommodate the variances in patient and external fixator size. Thus, as depicted in FIG. 7, the covering 10 is in the form of a fabric sheet 12 having closure elements or fasteners 14 at the free edges 12a, 12b of the sheet. The edges 12a, 12b may overlap in the region 13 with appropriate positioning of the closure elements 14. The closure elements 14 can be configured to allow variable overlap as necessary to wrap comfortably about the external fixation device.

Figure 8:
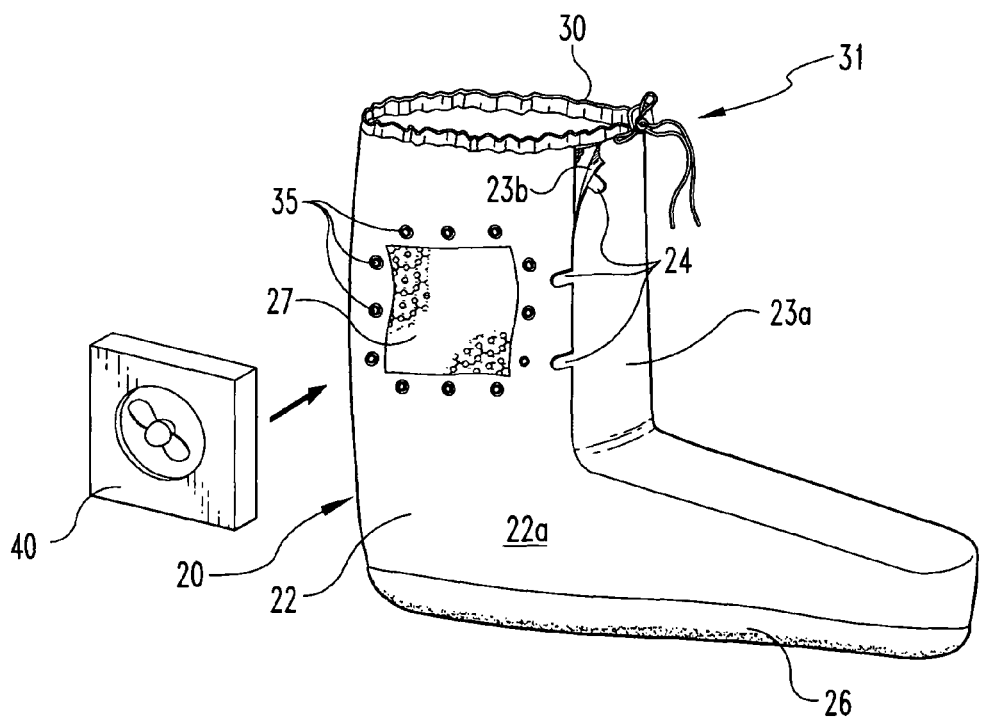
FIG. 8 is a perspective view of a protective and cosmetic covering according to another embodiment for use with an external fixator placed on a lower limb.
Figure 9:
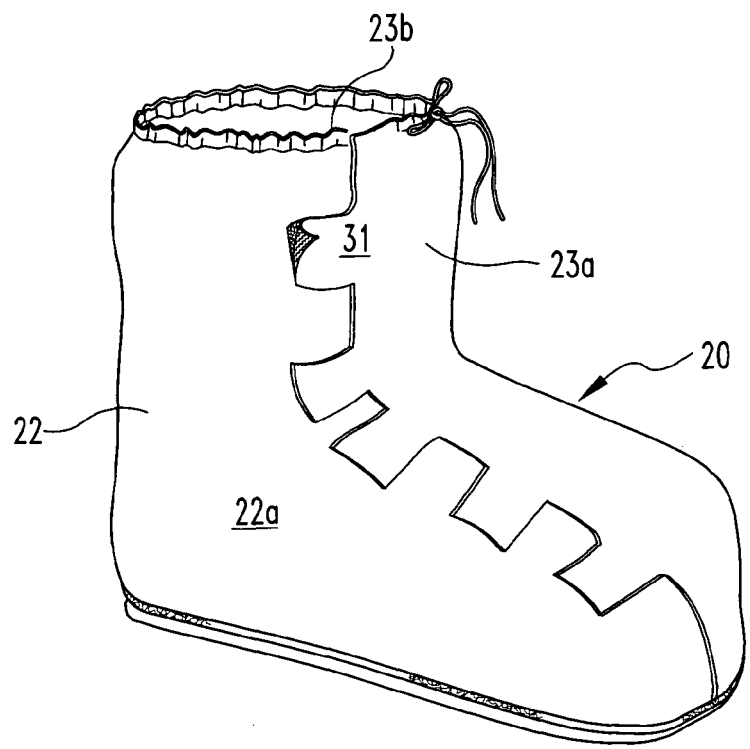
FIG. 9 is a perspective view of an alternative embodiment of a covering for use with an external fixator on the lower limb.

For the lower extremity covering 20 shown in FIG. 8, a fabric form 22 is shaped to encompass the foot and lower limb, with overlapping panels 23 and closure elements 24 of the type described above. The overlapping panels 23a, 23b accommodate variation in sizes of the external fixation device for the lower extremity. One type of closure element 24 employs hook and loop fasteners, as shown in FIG. 9. In this embodiment, the closure element may be adjustable to account for size variations in the external fixator. It is contemplated that the overlapping panels 23a, 23b are open and spread apart to allow access for the external fixator. Once the fixator is in position within the fabric form, the panels can be overlapped and attached by the closure elements 24.

Figure 13A:
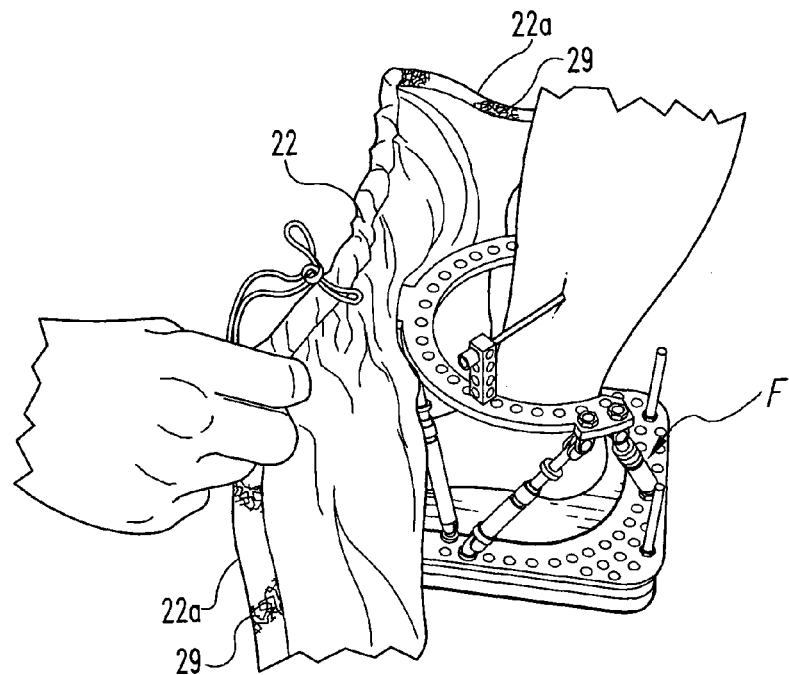
FIGS. 13a-b are perspective views of one embodiment of a protective covering being positioned around an external fixator on the lower limb.
Figure 13B:
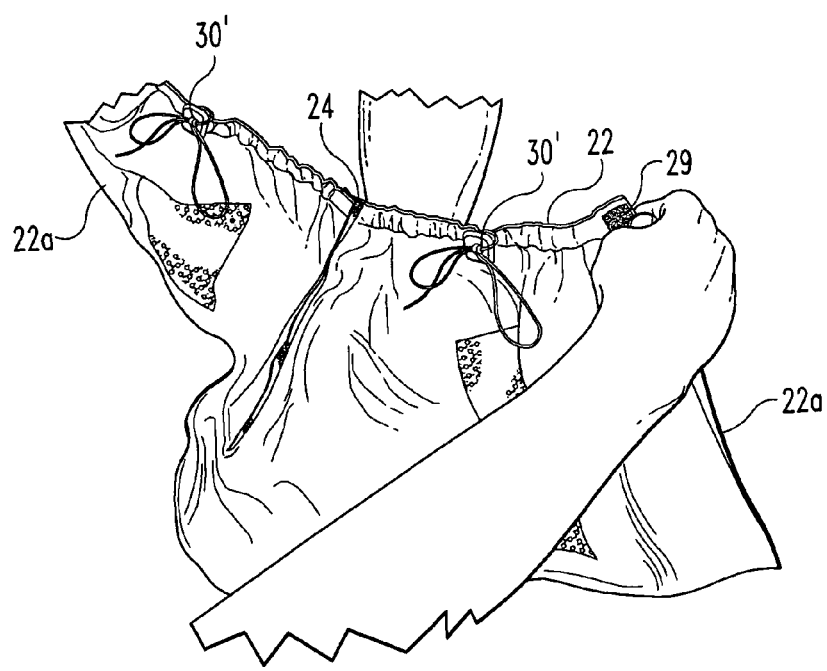

It is further contemplated that fabric form 22 may also be configured with the side panels 22a having additional closure elements 29 at a back portion of the covering 20 in conjunction with the panels 23a, 23b and closures 24, as illustrated in FIGS. 13a, 13b. With this construction, the entire fabric form 22 may be essentially laid open. Once the fixator is positioned within the form the side panels 22a can be brought together around the fixator until the closure elements 29 are properly aligned. This configuration provides the greatest degree of flexibility in applying the covering to an existing external fixator. It can be noted in the embodiment shown in FIGS. 13a,b that each side panel 22a includes a drawstring 30' that may be pulled and cinched to tighten the upper perimeter of each side panel individually. Thus, once the fabric form 22 is wrapped completely around the fixator F and the closures 24, 29 are fastened, the drawstrings 30' can be tightened to fully enclose the lower limb and fixator.

Figure 11:
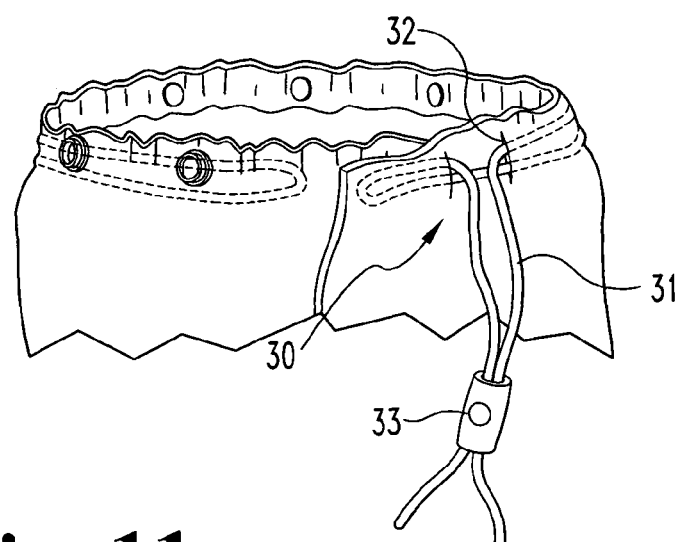
FIG. 11 is an enlarged perspective view of a drawstring feature of certain embodiments of the protective and cosmetic covering.
Figure 10:
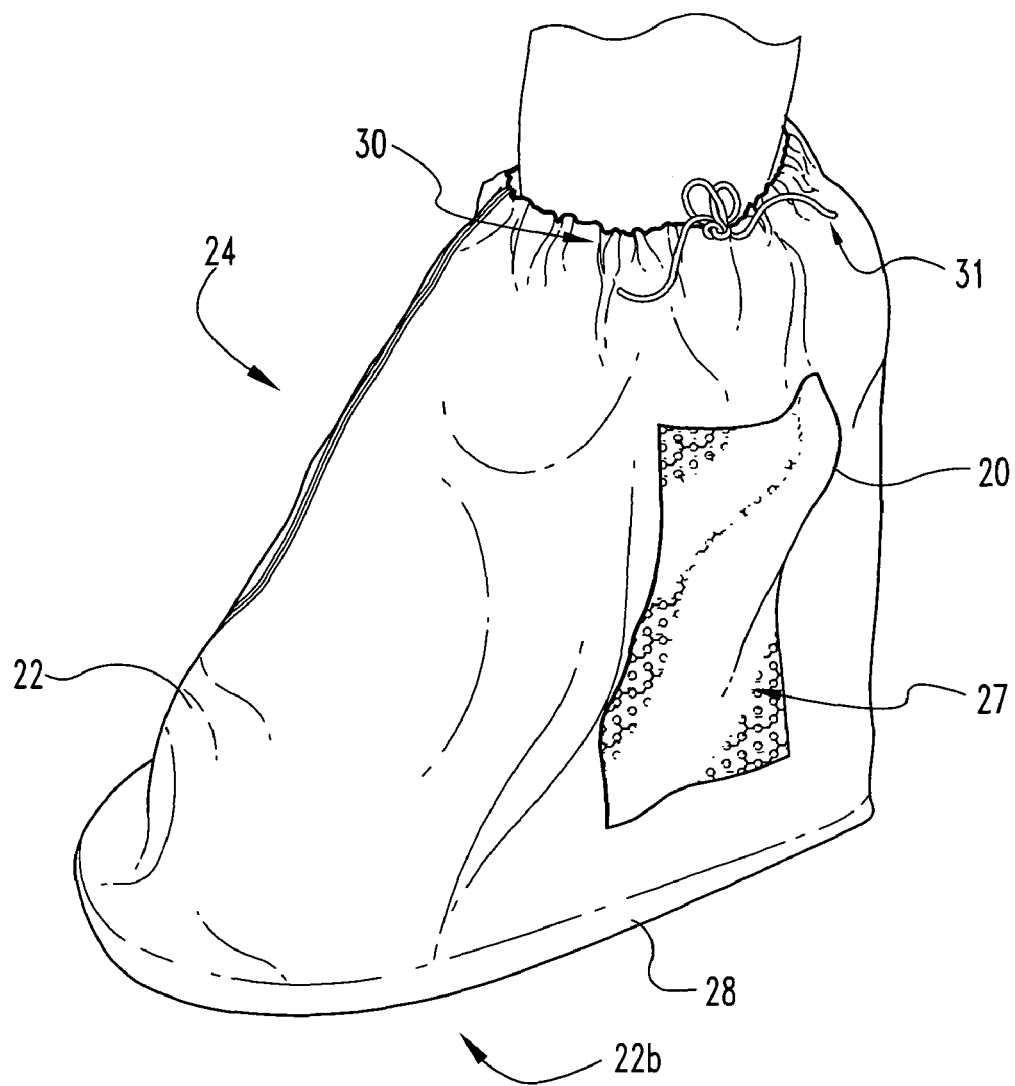
FIG. 10 is perspective view of a further embodiment of a covering with a footplate for use with an external fixator for the lower limb.

In one embodiment of the lower extremity covering 20, a rubber sole 26 may be attached to the fabric form 22, such as by gluing or sewing as is known in shoe construction. Alternatively, as depicted in FIGS. 10 and 11, a separate foot plate 28 may be provided in which the underside of the foot plate is configured to provide traction for the patient. A closure arrangement is provided between the perimeter 28a of the foot plate 28 and the lower edge 22b of the fabric form that allows selective removal of the foot plate. In one specific embodiment, this closure arrangement may comprise a hook and loop fastener strip fastened to perimeter 28a and to the inside of the lower edge 22b. Alternatively, the closure arrangement may include a zipper, snaps, or buttons, provided that the closure allows for easy removal by the patient.

In the preferred embodiments, the coverings 10, 20 are made of a washable material. Thus, the covering may be made of cloth or vinyl, or similar washable materials. An additional feature may be the addition of external pockets into which placards can be placed. The placards could include identification or artwork to personalize the cover. As a further alternative, the covering could be made from a material that easily allows permanent decoration, as in the case of patients writing on their casts.

In an alternative embodiment, the coverings 10, 20 may be formed of a waterproof fabric, such as neoprene, or a chemically treated fabric, such as treated nylon. The covering is thus configured to fully enclose the limb and external fixator. In another embodiment, the protective covering may be insulated. Thus, the fabric form 22 may be itself an insulating material. Alternatively, pockets may be incorporated into the fabric form into which sheets of insulating material may be inserted. The pockets would thus extend to substantially cover each side 22a of the fabric form 22. The insulating sheets are preferably not permanently affixed to the covering to allow for removal at the user's discretion in case of a climate change. Additionally, these same pockets may house cooling packets for warm environments. These same pockets may also provide a location for insertion of hard sheeting for protection from mechanical insult, as might occur during play time for the pediatric patient or at a sporting event.

In another feature of certain embodiments, the covering may provided with vents, such as vents 16 in the upper extremity covering 10 shown in FIG. 7, or vents 27 in the lower extremity covering 20, shown in FIGS. 8, 10. The vents allow air flow through the covering when wrapped around the upper or lower limb external fixation device. The vents are preferably in the form of an open mesh material. The vents may be provided with flaps that may be used to close the vents and temporarily fastened using a conventional fastener, such as a hook and loop fastener, snaps, buttons, or a zipper.

In certain embodiments, the covering may be provided with anchorage points 35 for attachment of mechanical ventilation means. For instance, a fan 40 may be fixed to the ventilation openings 27, as shown in FIG. 8, to enhance cooling by forced air flow. In very hot settings, this seemingly extreme measure may be necessary to prevent over-heating of the metallic fixation structure.

In another embodiment, the free end of the covering—i.e., the end/s not attached to the base plate for lower extremity models, or to a glove or wrist support for upper extremity models—may be secured to the fixator via, but not limited to, a drawstring closure similar to cinching closed a trash bag or laundry bag. Thus, in certain embodiments, a drawstring closure 19 for the upper limb covering 10, shown in FIG. 7, or closure 30 for the lower extremity covering 20, shown in FIGS. 8 and 10, may be provided that can be pulled tight about the open ends of the respective coverings 10, 20. The drawstring closures 19, 30 preferably contact the patient's extremity to, in effect, seal the covering about the arm or leg of the patient. The drawstring closures thus help seal the environment around the fixator F. Details of one embodiment of the drawstring closure 30 are shown in FIG. 11. The drawstring 31 may pass through a hem 32 at the open end of the covering and cinched tight using a ferrule 33.

Figure 12:
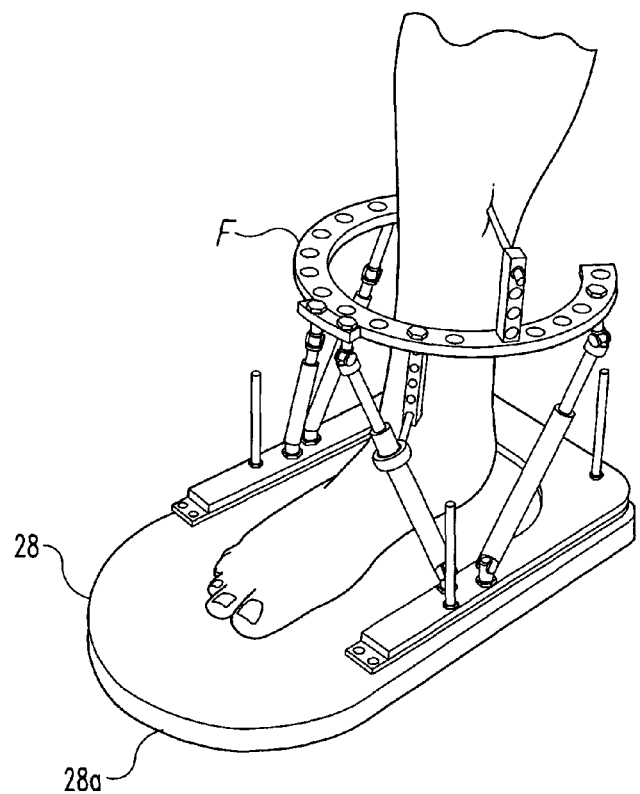
FIG. 12 is a perspective view of a footplate in accordance with certain disclosed embodiments for use with a lower limb external fixator.

For the lower extremity fixator cover 20 it may be desirable to fix the cover to a base plate in fixators that are attached to the foot to enable the patient to ambulate. In one embodiment of the invention, a base plate 27 will provide for fixation points to the fixator F itself, as illustrated in FIG. 12. There will be multiple arrangements or points of fixation to accommodate the many sizes and styles of fixators. These fixation points are oriented so as to not protrude through the underside of the base plate and interfere with ambulation, or outside the perimeter 27 of the base plate.

The base plate 27 is preferably covered with a soling material to provide for a slip-resistant surface. An additional embodiment will be to provide a cushion on the side of the base plate that abuts the foot. This cushion may be padded and made of a washable material.

Figure 14:
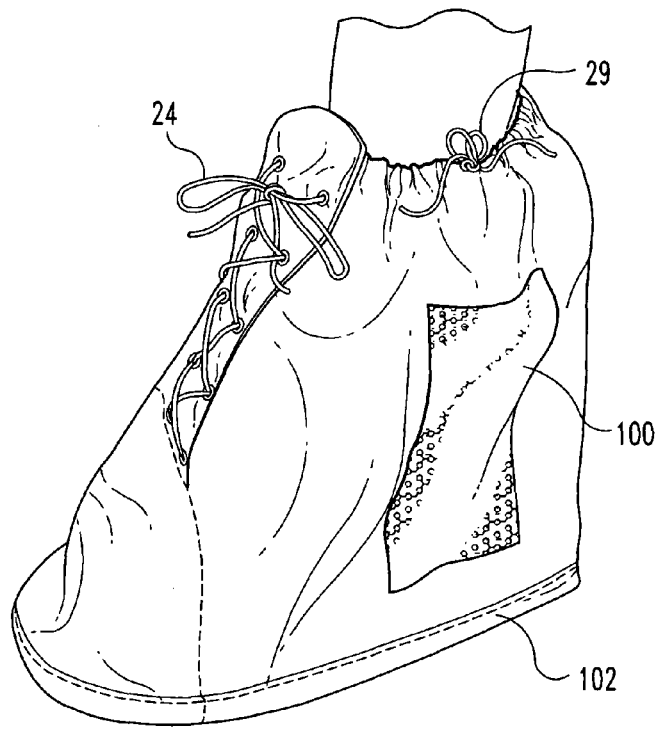
FIG. 14 is a perspective view of an alternative embodiment of a protective covering with particular aesthetic features.

The covering of the present invention may be optimized for aesthetic appearances. For instance, as shown in FIG. 14, the covering 100 may have the appearance of an oversized tennis shoe. The fabric form 102 may present the design features of a tennis show, along with the front and back closure elements 24, 29, which are shoelaces. In this embodiment, the fabric form may incorporate eyelets through which the shoelace closure elements are threaded to close the covering around the fixator. Alternatively, the fabric covering may be available in various colors or color schemes, such as of a college alma mater or favorite professional sports team.

The present invention contemplates a removable covering that can be secured about an external fixation device on the upper or lower extremity of a patient. The covering protects the fixation device while providing an aesthetic improvement to the limb while it mends. The covering is sized and configured to accommodate varying sizes of external fixation devices and uses readily engageable/releasable closure elements or fasteners to securely engage the covering about the extremity. In some embodiments, a drawstring closure may be provided at the open ends of the covering to tighten the end about the patient's limb. In other embodiments, ventilation features may be provided including vents with and without additional devices to generate air flow through the covering. In another embodiment of the invention, the covering for a lower extremity fixation device is configured to be removably attached to a foot plate. The foot plate itself may also be configured to support components of the fixation device.

What is claimed is:

1. A covering for an external fixator implanted into the limb of a patient, comprising:
    a fabric form sized and configured to substantially surround and enclose the external fixator said fabric form including a two panels having edges arranged for overlapping contact, wherein said fabric form is open at a lower perimeter;
    a footplate adapted to support an external fixator for a lower limb; and
    a closure arrangement at said edges arranged for overlapping contact, said closure arrangement configured to engage said edges together about the external fixator; said closure arrangement between said footplate and said lower perimeter.

2. The covering of claim 1, wherein said closure arrangement includes a hook and loop fastener strip disposed between said edges.

3. The covering of claim 1, wherein said closure arrangement includes a plurality of hook and loop fasteners disposed between said edges.

4. The covering of claim 1, wherein:
    said fabric form defines an opening through which the patient's limb extends when said edges are in overlapping contact; and
    said covering further includes a drawstring around said opening arranged to tighten said covering around the patient's limb at said opening.

5. The covering of claim 1, wherein said fabric form includes at least one ventilation opening.

6. The covering of claim 5, wherein said at least one ventilation opening includes a mesh screen covering the opening.

7. The covering of claim 5, wherein further comprising a fan mounted over said at least one ventilation opening.

8. The covering of claim 1, wherein said footplate includes means for mounting the external fixator thereto.

9. The covering of claim 1, wherein said fabric form is configured to provide an aesthetic appearance.

* * * * *